(12) United States Patent
Hofmann

(10) Patent No.: US 7,661,295 B2
(45) Date of Patent: Feb. 16, 2010

(54) METHOD FOR COUPLING A GAS CHROMATOGRAPHY DEVICE TO AN NMR SPECTROMETER AND ASSOCIATED APPARATUS

(75) Inventor: Martin Hofmann, Rheinstetten (DE)

(73) Assignee: Bruker Biospin GmbH, Rheinstetten (DE)

( * ) Notice: Subject to any disclaimer, the term of this patent is extended or adjusted under 35 U.S.C. 154(b) by 139 days.

(21) Appl. No.: 11/798,059

(22) Filed: May 10, 2007

(65) Prior Publication Data

US 2007/0266768 A1 Nov. 22, 2007

(30) Foreign Application Priority Data

May 17, 2006 (DE) .................. 10 2006 022 953

(51) Int. Cl.
*G01N 1/00* (2006.01)
(52) U.S. Cl. .................................................. 73/23.41
(58) Field of Classification Search ............... 73/23.41, 73/23.42; 324/308
See application file for complete search history.

(56) References Cited

U.S. PATENT DOCUMENTS

| | | | |
|---|---|---|---|
| 5,283,036 A | | 2/1994 | Hofmann |
| 5,970,804 A | * | 10/1999 | Robbat, Jr. ............... 73/863.12 |
| 6,614,228 B2 | | 9/2003 | Hofmann |
| 6,968,729 B1 | * | 11/2005 | Karlsson et al. ............ 73/23.41 |
| 7,256,052 B2 | * | 8/2007 | Coute et al. .................. 436/181 |
| 2006/0054544 A1 | | 3/2006 | Roenneburg |

FOREIGN PATENT DOCUMENTS

EP 1 202 054 5/2002

OTHER PUBLICATIONS

"Preparative Fraction Collector PFC", Gerstel GmbH, Muelheim an der Ruhr, Germany, Dec. 1999.

* cited by examiner

*Primary Examiner*—John Fitzgerald
(74) *Attorney, Agent, or Firm*—Paul Vincent

(57) ABSTRACT

A method for coupling a gas chromatograph (21) to an NMR spectrometer, wherein the carrier gas present at the outlet of a separating column (23) of the gas chromatograph (21) including a sample contained in the carrier gas is supplied via a heated transfer line (1) to a collecting device (2) for the sample contained in the carrier gas, is characterized in that the carrier gas containing the sample is introduced into a collecting liquid (8) in the collecting device (2), and the sample is collected in the collecting liquid (8), wherein the collecting liquid (8) is suitable as an NMR solvent for the sample. The sample loss of the coupling method is reduced.

18 Claims, 3 Drawing Sheets

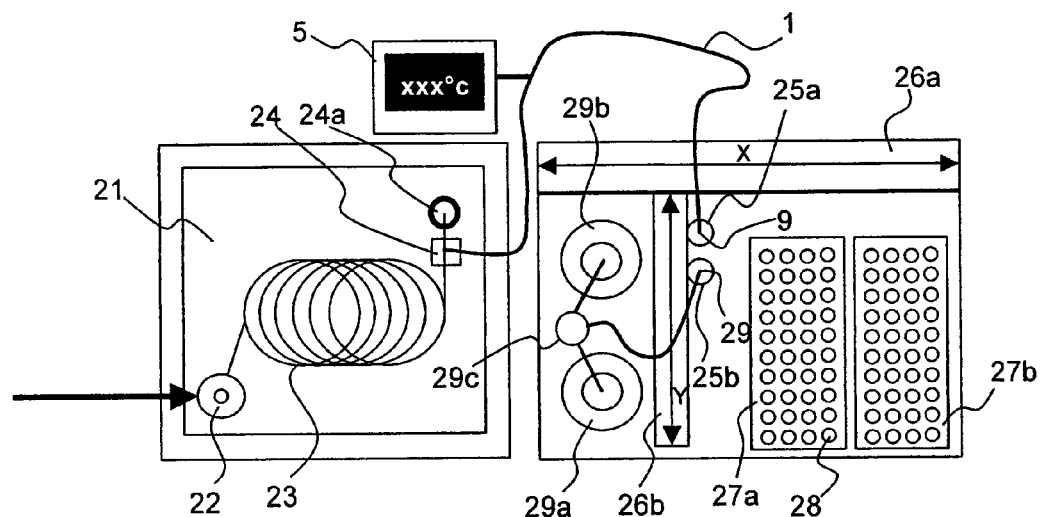
Fig. 2a
Fig. 2b
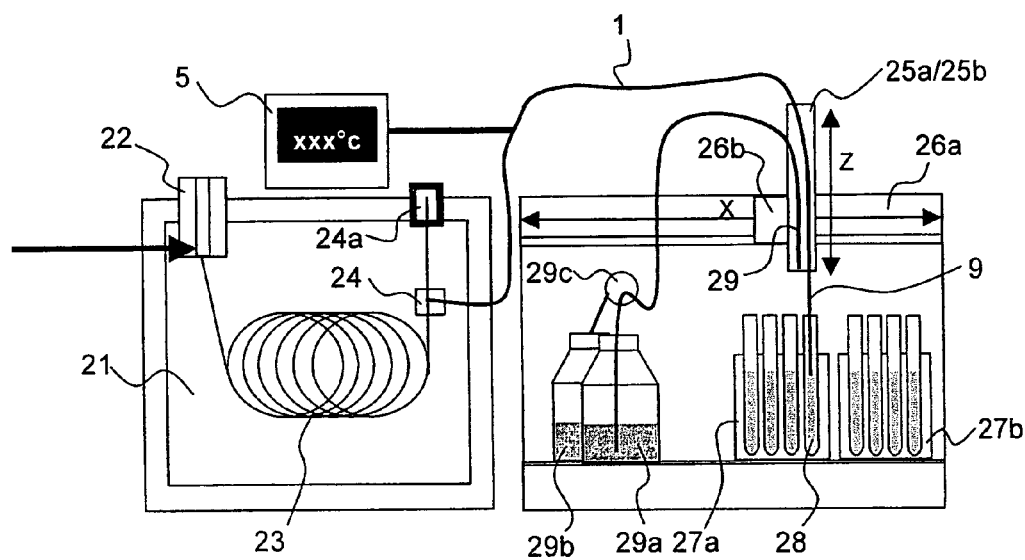

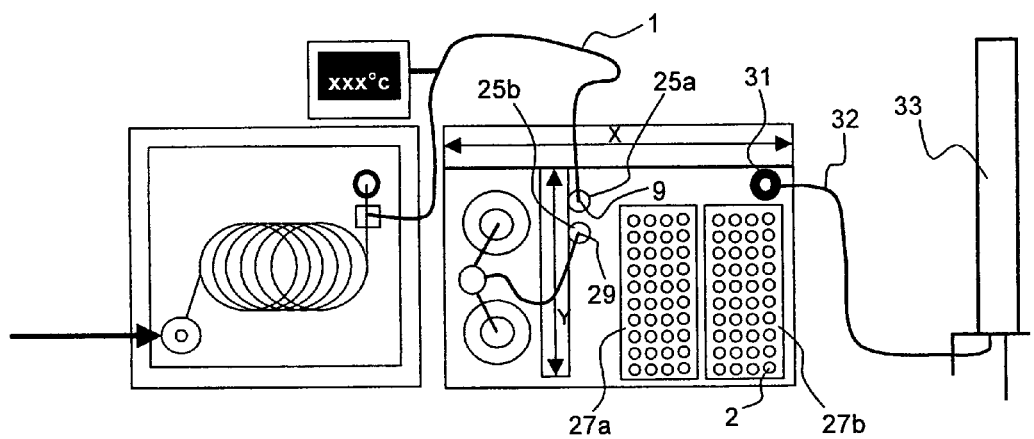
Fig. 3a
Fig. 3b
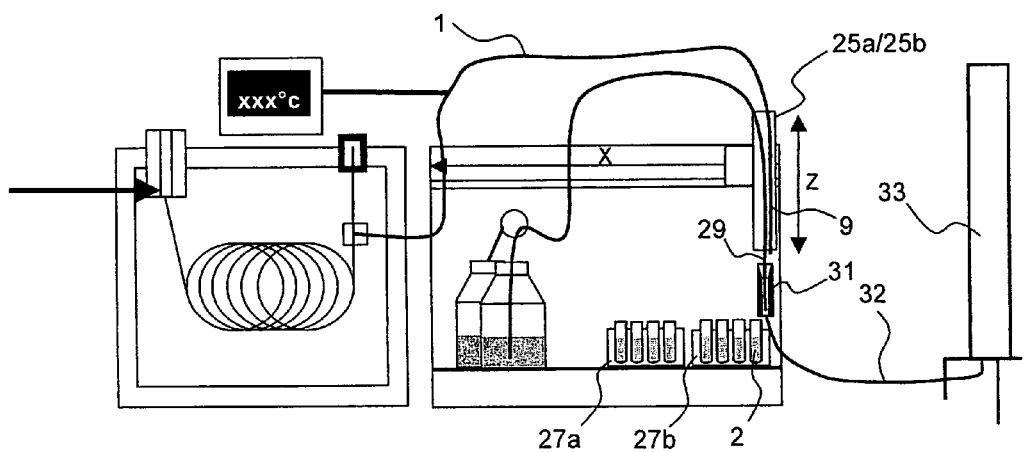

METHOD FOR COUPLING A GAS CHROMATOGRAPHY DEVICE TO AN NMR SPECTROMETER AND ASSOCIATED APPARATUS

This application claims Paris Convention priority of DE 10 2006 022 953.3 filed May 17, 2006 the complete disclosure of which is hereby incorporated by reference.

BACKGROUND OF THE INVENTION

The invention concerns a method for coupling a gas chromatograph to an NMR spectrometer, wherein the carrier gas present at the outlet of a separating column of the gas chromatograph, including a sample contained in the carrier gas, is supplied via a heated transfer line to a collecting device for the sample contained in the carrier gas.

A method of this type is e.g. used with the "preparative fraction collector PFC" (Präparativer Fraktioniersammler PFC) of the company Gerstel GmbH & Co. KG, Mülheim an der Ruhr (see their manual, issued December 1999).

Nuclear magnetic resonance (NMR) spectroscopy is an important method for the analysis of chemical substances. The behavior of the nuclear spins of the substance to be analyzed is thereby measured during excitation in a strong magnetic field.

The test samples to be investigated are often a mixture of the most different of chemical substances. When all components of the mixture are measured at the same time, the resonance lines of the substances overlap. This complicates determination of the individual chemical substances.

In order to simplify determination of the individual chemical substances, the test sample to be investigated is conventionally separated prior to the NMR measurement. One of these separating methods is gas chromatography (GC). GC is used, in particular, for separating test samples that contain non-polar substances. The test sample is introduced into a separating column through which a carrier gas (e.g. nitrogen gas) flows. The separating column is then slowly heated, and the individual substances of the test sample gradually pass over into the gaseous phase and are transported away by the carrier gas. Below, the substance(s) contained in the carrier gas is/are referred to as the sample. The sample is conventionally initially collected, subsequently dissolved in a solvent, and measured in the NMR spectrometer.

A heated transfer line is connected to the separating column of the PFC apparatus of the company Gerstel and is guided to six collecting tubes via a distributor valve. The collecting tubes are designed as open U-shaped tubes which are cooled in their lower region. The sample condenses out in this lower region. When a sufficient amount of substance has condensed (which usually requires multiple feeding of the separating column and heating cycles), the sample is manually washed out of the collecting tube with a solvent, concentrated, transferred to an NMR sample tube, and is subsequently measured.

In this conventional method, a relatively large amount of sample is lost between the separating column and the NMR spectrometer, initially through the open collecting tube. The sample is not completely condensed on the wall of the collecting tube, in particular, when the collecting tubes are short, but part thereof exits through the open end. Sample substance is also lost when the sample is washed out of the collecting tube and filled into an NMR sample tube. If only little test sample is available, i.e. the loss of sample cannot be compensated for through accumulation over several GC runs, sample loss deteriorates the signal-to-noise ratio of the NMR measurement, or even renders NMR measurement impossible.

Since both the distributor valve and the transfer line must be heated in order to prevent condensation of the sample before it reaches the collecting tube, or even clogging of the line, the number of collecting tubes is also usually limited (in the system "PFC", limited to six collecting tubes).

It is the underlying purpose of the present invention to provide a method for coupling a gas chromatograph to an NMR spectrometer with which the sample loss is reduced. Fundamentally, a method of this type should also considerably increase the number of possible collecting locations and reduce manual interactions.

SUMMARY OF THE INVENTION

This object is achieved by a method of the above-mentioned type which is characterized in that the carrier gas that contains the sample is introduced into a collecting liquid in the collecting device, and the sample is collected in the collecting liquid, the collecting liquid being suitable as an NMR solvent for the sample.

In the inventive method, the gaseous sample is brought into direct contact with the collecting liquid immediately after leaving the heated transfer line. A typical sample is thereby practically completely bound in the liquid. The sample may thereby, in particular, (preferably) be dissolved in the collecting liquid or the sample can be precipitated in the collecting liquid. Nearly no sample is lost during filling of the collecting device with the sample.

The collecting liquid is selected to serve as an NMR solvent for the sample. In particular, there is a sufficiently small overlap between the resonance lines of the NMR solvent and the resonance lines of the chemical substance(s) or expected chemical substance(s) in the sample. The sample which is bound in the collecting liquid is easy to handle and transfer without loss. In particular, the sample contained in the collecting liquid can be directly supplied to an NMR spectrometer and be measured, if desired, after adding further solvents or NMR standards. In accordance with the invention, the sample need not be washed out of a collecting tube. A larger portion of the sample can therefore be utilized for the NMR measurement.

The invention eliminates the two main causes for sample loss during coupling between the GC and NMR spectrometer in accordance with prior art (i.e. small condensation yield and washing-out loss).

Introduction of the carrier gas, including sample, into exchanged collecting devices is easy, since the collecting liquid in each collecting device displays a sealing effect relative to the sample contained in the carrier gas. Due to the simple exchange, any number of collecting devices may, in principle, be used and the exchange may be performed automatically.

In one preferred variant of the inventive method, an end section of the heated transfer line is immersed into the collecting liquid, and the temperature $T_{end}$ of the immersed end section of the heated transfer line is maintained below the boiling temperature $T_S$ of the collecting liquid. Immersion of the end section ensures that the total amount of sample that leaves the transfer line reaches the collecting liquid. Loss of collecting liquid due to evaporation is also prevented. In order to limit or prevent cooling of the transfer line at the immersed end section, the collecting liquid may be heated, preferably to the temperature of the transfer line (to the extent permitted by the boiling point of the collecting liquid).

In another preferred method variant, any point of the heated transfer line is maintained at a temperature $T_{leit}$ which is larger or equal to the instantaneous separating temperature $T_{trenn}$ of the gas chromatograph. This prevents clogging of the transfer line due to precipitation (condensation) of the sample in the transfer line. In the simplest case, the transfer line is held at a constant temperature which is greater than or equal to the maximum separating temperature of the gas chromatograph.

In one particularly preferred method variant, an NMR sample tube is used as a collecting device. This avoids any refilling prior to the NMR measurement, thereby providing a maximum amount of sample for the NMR measurement.

In another advantageous method variant, dimethyl sulfoxyde (DMSO) is used as a collecting liquid. DMSO has a high boiling point (approximately 189° C. at normal pressure) and can therefore also be used with high separating temperatures or high temperatures of the end section of the transfer line.

In another advantageous variant of the inventive method, the collecting device is only partially filled with collecting liquid during introduction of the carrier gas containing the sample, and after introduction of the carrier gas containing the sample, the collecting device is filled up with an additional liquid, wherein the additional liquid is suited as an NMR solvent for the sample. The additional liquid can e.g. dissolve precipitation of the sample in the collecting liquid. The additional liquid can have any boiling point, in particular, a relatively low boiling point compared to the collecting liquid.

In another preferred method variant, the sample, which is dissolved in the collecting liquid and optionally in the additional liquid, is supplied via a feed capillary to an NMR flow head of an NMR spectrometer to perform an NMR measurement. Nearly no sample material is lost due to the direct, easily automated transfer of the dissolved sample from the collecting device to the measuring head.

One particularly preferred method variant comprises several collecting devices, which collect samples in a collecting liquid in a time sequence. Individual fractions of the measuring sample can be separately stored in the collecting devices, and be enriched, if required. Fractioning facilitates identification of individual chemical substances. Within the scope of the invention, the number of collecting devices which can be used is essentially unlimited.

In a preferred further development of this method variant, the collecting devices are disposed on a carrier frame in the form of a sample library and are approached by a robot arm. The robot arm is used, in particular, for relocating the heated transfer line from one collecting device to another collecting device. The robot arm and the sample library facilitate automation of the NMR analysis (auto sampler function).

In a further variant of this further development, the approach to the collecting devices is controlled by a sensor (GC detector) at the output of the separating column of the gas chromatograph. The sensor detects whether a sample is contained in the carrier gas at the instantaneous separating temperature or whether only carrier gas escapes from the separating column. As long as only carrier gas escapes from the separating column, the transfer line can be kept outside of the collecting devices. As soon as the sensor detects a sample, collection of sample is initiated. For this reason, only as many collecting devices are required as sample fractions present. Collecting devices may alternatively be associated with fixed separating temperatures or separating temperature intervals.

In a preferred method variant, a substance which shall be measured several times is supplied to the gas chromatograph, the substance to be measured is separated with the gas chromatograph, and the sample is concentrated in the collecting liquid of a collecting device through several separating cycles of the gas chromatograph. This improves the signal-to-noise ratio during subsequent measuring of the concentrated samples in the NMR spectrometer.

The present invention also concerns an apparatus for coupling a gas chromatograph to an NMR spectrometer, comprising a gas chromatograph with a separating column, whose outlet is connected via a heatable transfer line to a collecting device for a sample contained in the carrier gas. The apparatus is characterized in that the collecting device contains a collecting liquid, wherein the collecting liquid is suitable to collect the sample and is an NMR solvent for the sample, wherein the heatable transfer line terminates within the collecting liquid. The sample can be practically completely collected in the collecting liquid, and is available in large amounts for NMR investigation.

In a preferred embodiment of the inventive apparatus, the collecting device is designed as an NMR sample tube. The NMR sample tube can be directly inserted into an NMR spectrometer, and refilling of the sample collected in the collecting liquid is not required.

In another preferred embodiment, the collecting liquid is DMSO. Dimethyl sulfoxide has a high boiling point (compared to other NMR solvents) and can therefore also be used at high temperatures of an immersed end section of the transfer line.

In another preferred embodiment, several collecting devices are provided which are disposed on a carrier frame, and a robot arm is provided for approaching the collecting devices. The robot arm and the carrier frame (in particular, being part of a sample library) can automate filling of the collecting devices. The robot arm may be used, in particular, for relocating the heatable transfer line.

In a preferred further development of this embodiment, a liquid transfer needle is provided which can be moved using the robot arm, and at least one liquid container is provided for supplying the liquid transfer needle. In this further development, the collecting devices can be automatically supplied with a liquid.

In an advantageous further development thereof, a liquid container is provided for the collecting liquid and/or a liquid container is provided for an additional liquid, wherein the additional liquid is suited as an NMR solvent for the sample, and/or a liquid container is provided for an NMR standard. The collecting liquid can be easily provided in the collecting devices using the robot arm, the additional liquid can be filled up in the collecting devices using the robot arm, or the NMR standard can be added to the collecting devices. Essentially the entire NMR preparation can thereby be performed with the inventive apparatus.

Further advantages of the invention can be extracted from the description and the drawing. The features mentioned above and below may be used in accordance with the invention either individually or collectively in arbitrary combination. The embodiments shown and described are not to be understood as exhaustive enumeration rather have exemplary character for describing the invention.

The invention is shown in the drawing and explained in detail with reference to embodiments.

BRIEF DESCRIPTION OF THE DRAWING

FIG. 2a shows a schematic plan view of a first embodiment of an inventive apparatus;

FIG. 2b shows a schematic side view of the apparatus of FIG. 2a in a position of a robot arm for filling an NMR tube;

FIG. 3a shows a schematic view of a second embodiment of an inventive apparatus with a feed capillary to an NMR flow head;

FIG. 3b shows a schematic side view of the apparatus of FIG. 3a in a position of a robot arm for filling an injection connection.

DESCRIPTION OF THE PREFERRED EMBODIMENT

Figure 1:
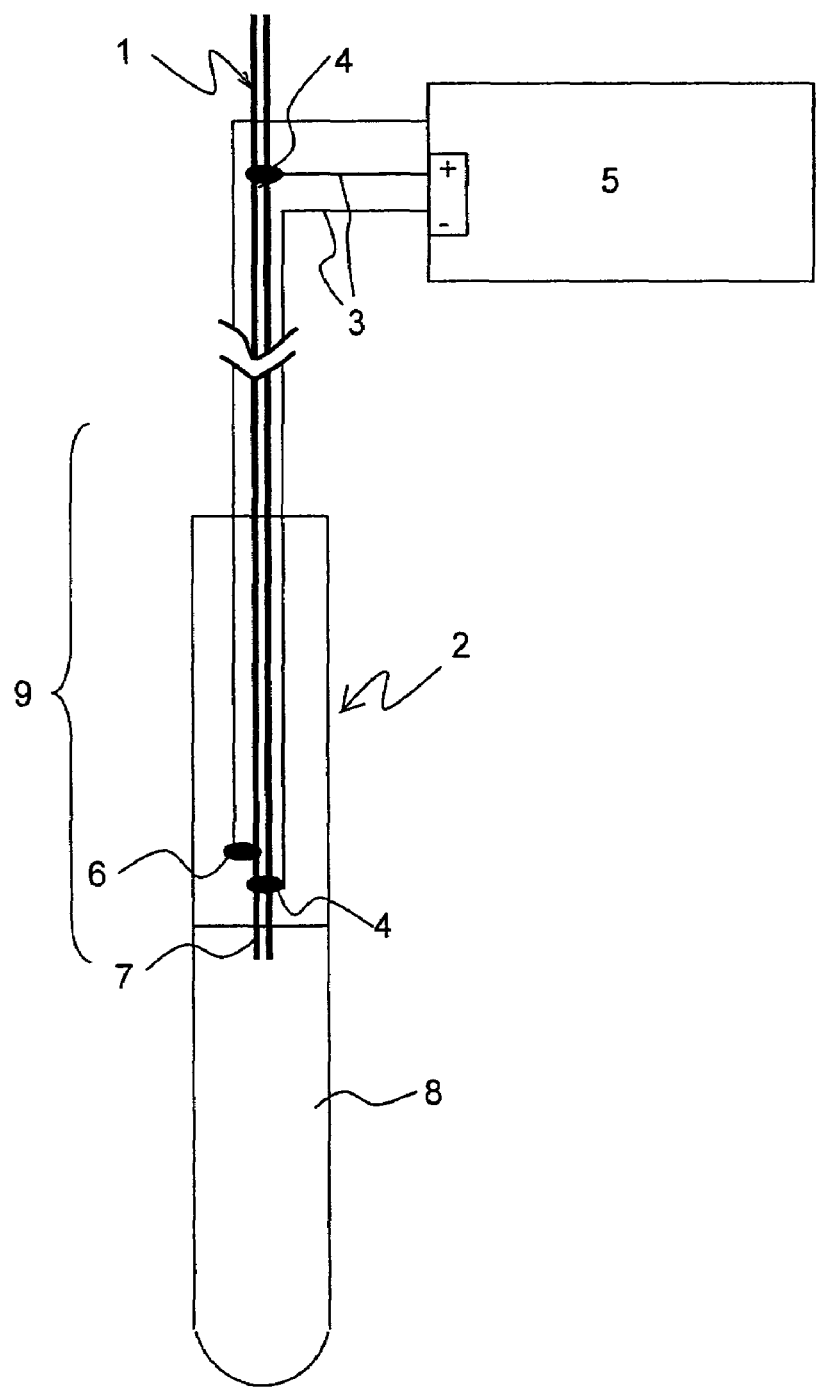
FIG. 1 shows a schematic view of a heatable transfer line which opens into a collecting liquid in a collecting device in accordance with the invention.

FIG. 1 schematically shows a heated transfer line 1 and a collecting device 2 for use of the inventive method and as part of an inventive apparatus.

The heated transfer line 1 is at least partially produced from an electrically conducting material, e.g. stainless steel or copper. The electrically conducting material thereby covers e.g. an inner capillary of quartz glass which is chemically inert to solvents and substances in a sample. The electrically conducting material can be exposed to an electric current using electric feed lines 3 and electric contacts 4, which heats the transfer line 1 by ohmic heating power. The electric current is thereby provided and controlled by a controller 5. The controller 5 is connected to a temperature sensor 6 for monitoring the instantaneous temperature $T_{leit}$ of the transfer line 1. The temperature sensor 6 is disposed in the vicinity of a lower end section 7 of the electric transfer line 1, since the transfer line 1 usually has a minimum temperature in the vicinity of the end section 7, wherein the risk of clogging of the transfer line due to sample condensated in the transfer line 1 is at a maximum. The electric heating current in the transfer line 1 is determined using the measured $T_{leit}$ and by a comparison with a desired temperature of the transfer line 1, e.g. using a PID regulation program.

The end section 7 of the transfer line 1 is immersed into a collecting liquid 8 which fills approximately half of the collecting device 2. When carrier gas and a sample contained in the carrier gas flow from the opening of the end section 7 of the transfer line 1, the sample contacts the collecting liquid 8 and is bound therein, e.g. precipitated. During flow, sample concentrates in the collecting liquid 8. After termination of sample concentration, the collecting device can be filled with an additional liquid, e.g. to dissolve a precipitated sample prior to an NMR measurement.

The immersion depth of the opening of the transfer line 1 into the collecting liquid 8 is preferably small (e.g. 1 to 2 mm) in order to minimize any cooling of the end section 7 by the collecting liquid 8. Excessive cooling could clog the opening of the transfer line 1. Moreover, the temperature $T_{end}$ of the end section 7 is below the boiling point of the collecting liquid 8 in order to prevent local evaporation of the collecting liquid 8.

The heatable transfer line 1 is rigid in a handling section 9 which surrounds the end section 9 and a part of the transfer line 1 facing the end section 9. The handling section 9 is e.g. designed as a needle and can be moved in three orthogonal spatial directions x, y, z by a robot arm (not shown).

FIG. 2a shows a first embodiment of an inventive apparatus for coupling a gas chromatograph 21 to an NMR spectrometer.

A test sample (which typically contains a plurality of chemical substances) and carrier gas may be supplied via an inlet 22 to a separating column 23. The separating column 23 is slowly heated and individual components of the test sample previously inserted into the separating column 23 gradually pass over into the gaseous phase and are transported away by the permanent carrier gas flow. The carrier gas is selected to be chemically inert to the test sample.

The carrier gas that carries along the sample, passes through a splitter 24 at the outlet of the separating column 23, and into a heated transfer line 1. The temperature $T_{leit}$ of the transfer line 1 is controlled via the control means 5 and is, in particular, always kept at a temperature above the instantaneous separating temperature $T_{trenn}$ in the separating column 23.

The heatable transfer line 1 is guided to a holder 25a which can be horizontally moved by a motor in the x and y directions along guidances 26a, 26b. A handling section 9 of the transfer line 1 is held in the holder 25a and can be vertically moved in z direction by a motor, i.e. the handling section 9 can be extended and retracted (compare FIG. 2b with extended handling section 9). The directions of motion x, y, z form the degrees of freedom of a "robot arm" for the handling section 9.

The holder 25a including handling section 9 can be moved, in particular, via two carrier frames 27a, 27b, which each contain 4×10 NMR tubes 28 in an upright position (i.e. with the opening facing the top), thereby forming one sample library each. The NMR tubes 28 have markings, e.g. bar codes to distinguish them.

The holder 25a may thereby be moved over each individual NMR tube 28 in the carrier frames 27a, 27b. This ensures that samples which are subsequently released in the gas chromatograph 21 can be collected in different NMR tubes 28. Start and termination of release of a new fraction of the test sample can be detected via a sensor 24a in the gas chromatograph 21. While no sample is being released, the handling section 9 can be moved to a parking position outside of the NMR tubes 28 or the gas flow can be guided into a flue or waste container using a valve (not shown).

An additional holder 25b can also be moved using the guidances 26a, 26b. A liquid transfer needle 29 is disposed therein such that it can be vertically displaced in the z direction (compare FIG. 2b which shows the liquid transfer needle in the retracted state). The liquid transfer needle 29 can supply an NMR solvent from one of two liquid containers 29a, 29b into an NMR tube 28. The liquid container, from which liquid is removed, can be selected by a switch-over valve 29c which can be automatically driven. A small pump (not shown) is provided in the additional holder 25b. As an alternative to switching over, each liquid container may have its own liquid transfer needle with pump, which can be moved in the z direction by a motor.

The liquid container 29a contains e.g. a collecting liquid for introduction into the NMR tube 28, whereas the liquid container 29b contains an NMR standard with resonance lines at known positions.

In the illustrated embodiment, the holder 25a and the additional holder 25b are commonly moved in parallel by the robot arm. Alternatively, only one common holder for the handling section 9 and liquid transfer needle 29 may be provided, which is moved by the robot arm and in which the handling section 9 (gas transfer needle) and liquid transfer needle 29 are each individually movable in the z direction by a motor.

FIG. 2b shows the apparatus of FIG. 2a, wherein the holder 25a can be moved by the robot arm over an NMR tube 28, and the handling section 9 of the transfer line 1 is just immersed into the collecting liquid 8 in the NMR tube 28. Towards this end, the handling section 9 is extended downwardly. In this position, sample is being collected in the NMR tube 28, however, the liquid needle 29 is just being retracted to the top. The outer diameter of the handling section 9 is smaller than the inner diameter of an NMR tube 28.

When the sensor 24a detects the end of a sample, the handling section 9 can be retracted and the holder 25a can be moved to another NMR tube. At the latest, when the sensor 24a detects the next sample, the handling section 9 is extended again and immersed into the collecting liquid. In accordance with the invention, the change between the NMR sample tubes is fully automated.

The liquid transfer needle 29 or the handling section 9 (gas transfer needle) can be used to mix (stir) the content of an NMR tube 28 to improve homogeneity.

The complete NMR sample preparation can be performed directly in an NMR tube 28 using the inventive apparatus, in particular, the liquid transfer needle 29. The NMR tubes 28 which contain collecting liquid enriched with sample, can be moved manually or mechanically to an NMR spectrometer, where their content is directly measured.

FIGS. 3a and 3b show an embodiment of an inventive apparatus similar to FIG. 2a and 2b, which is designed as a flow injection system.

The samples contained in the carrier gas (e.g. $N_2$ or argon) need not be disposed into NMR tubes but can be disposed into conventional collecting devices 2.

The apparatus has an injection port 31 which is connected to an NMR flow head 33 of an NMR spectrometer via a feed line capillary 32. Liquid which is inserted into the injection port is supplied to the NMR flow head and can then be measured in the NMR spectrometer.

When a sufficient amount of sample has been concentrated in the collecting liquid of a collecting container 2 and optionally further liquids have been added, the liquid transfer needle 29 suctions the content (or part of the content) of a collecting device 2. The transfer needle 29 is subsequently moved to the injection port 31 (see FIG. 3b) and ejects the content. The contained sample including NMR solvents is supplied to the NMR spectrometer and measured. Washing out of a sample or refilling into another sample container is not required. This minimizes sample loss.

The inventive method or the inventive apparatus can be used, in particular, for investigating perfume components, flavor substances, cosmetic raw materials or flavoring. The collecting liquid and/or other NMR solvents which are used within the scope of the invention are preferably deuterized. The robot arm can be used as an "auto sampler" for several separation processes of the gas chromatograph, in order to obtain sufficient concentration of the sample in each collecting device. In a suitable design of the apparatus, the robot arm may also be used to supply the gas chromatograph with the measuring sample. The invention can be used with any type of gas chromatograph. The only information that must be transferred between the gas chromatograph and the auto sampler is initiation of separation and optionally a signal of the sample detector.

I claim:

1. A method for coupling a gas chromatograph to an NMR spectrometer, the method comprising the steps of:
   a) supplying a carrier gas from an outlet of a separating column of the gas chromatograph, including a sample contained in the carrier gas, via a heated transfer line to a collecting device;
   b) inserting the carrier gas, containing the sample, into a collecting liquid in the collecting device to collect the sample in the collecting liquid, wherein the collecting liquid is suitable as an NMR solvent for the sample; and
   c) performing an NMR measurement in an NMR spectrometer of the sample collected in the collecting liquid.

2. The method of claim 1, wherein an end section of the heated transfer line is immersed into the collecting liquid, a temperature $T_{end}$ of the immersed end section of the heated transfer line being kept below a boiling temperature $T_S$ of the collecting liquid.

3. The method of claim 1, wherein the heated transfer line is kept at a temperature $T_{leit}$ which is larger than or equal to an instantaneous separating temperature $T_{trenn}$ of the gas chromatograph.

4. The method of claim 1, wherein the collecting device comprises an NMR sample tube.

5. The method of claim 1, wherein the collecting liquid comprises dimethyl sulfoxyde (DMSO).

6. The method of claim 1, wherein a substance, which is to be measured several times, is supplied to and separated with the gas chromatograph, wherein the sample is concentrated in the collecting liquid of the collecting device over several separating cycles of the gas chromatograph.

7. The method of claim 1, wherein the collecting device is partially filled with collecting liquid during introduction of the carrier gas containing the sample, and, after introduction of the carrier gas containing the sample, the collecting device is filled up with additional liquid, wherein the additional liquid is suitable as an NMR solvent for the sample.

8. The method of claim 7, wherein the dissolved sample is supplied via a feed capillary to an NMR flow head of an NMR spectrometer to perform an NMR measurement.

9. The method of claim 1, wherein several collecting devices are provided which sequentially collect samples in a collecting liquid.

10. The method of claim 9, wherein the collecting devices are disposed on a carrier frame as a sample library for approach by a robot arm.

11. The method of claim 10, wherein approach to the collecting devices is controlled by a sensor at an outlet of the gas chromatograph separating column.

12. A device for coupling a gas chromatograph to an NMR spectrometer the device comprising:
   means for supplying a carrier gas from an outlet of a separating column of the gas chromatograph, including a sample contained in the carrier gas, via a heated transfer line to a collecting device; and
   means for inserting the carrier gas containing the sample into a collecting liquid in the collecting device to collect the sample in the collecting liquid, wherein the collecting liquid is suitable as an NMR solvent for the sample.

13. The device of claim 12, wherein the heated transfer line feeds into the collecting liquid.

14. The device of claim 12, wherein the collecting device comprises an NMR sample tube.

15. The device of claim 12, wherein the collecting liquid is DMSO.

16. The device of claim 12, wherein several collecting devices are disposed on a carrier frame for approach by a robot arm.

17. The device of claim 16, further comprising a liquid transfer needle structured for movement by the robot arm and at least one liquid container for feeding the liquid transfer needle.

18. The device of claim 17, wherein a liquid container is provided for the collecting liquid, a liquid container is provided for an additional liquid which is suited as an NMR solvent for the sample, and/or a liquid container is provided for an NMR standard.

* * * * *